United States Patent [19]
Lee et al.

[11] Patent Number: 5,434,324
[45] Date of Patent: Jul. 18, 1995

[54] PREPARATION OF ALKYLCYCLOPENTADIENES

[75] Inventors: John Y. Lee; Meng-Sheng Ao, both of Baton Rouge, La.

[73] Assignee: Albemarle Corporation, Richmond, Va.

[21] Appl. No.: 137,683

[22] Filed: Oct. 15, 1993

[51] Int. Cl.⁶ .......................... C07C 1/20; C07C 1/207
[52] U.S. Cl. .................... 585/357; 585/358; 585/638
[58] Field of Search ............... 585/357, 358, 359, 375, 585/376, 601, 603, 606, 609, 638, 639

[56] References Cited

PUBLICATIONS

Weber et al, Enantiomerically Pure Tertiary Alcohols by TADDOL-Assisted Additions to Ketones-or How to Make a Grignard Reagent Enantioselective, Angew. Chem., Int, Ed., vol. 31, 1992, pp. 84–86.

Morrison et al, Organic Chemistry, 4th Ed., Ally and Bacon Inc., 1983, pp. 281 and 519.

Deno, N. C., et al., "Carbonium Ions, XI, Nuclear Magnetic Resonance Spectra of the Aliphatic Alkenyl Cations", J. Am. Chem. Soc. 85, 2991, Oct. 5, 1963.

Ford, W. T., "Cycloaddition of Benzyne to Substituted Cyclopentadienes and Cyclopentadienyl Grignard Reagents", J. Org. Chem., vol 36, No. 25 (1971) pp. 3979–3987.

McLean, S., et al., "Substitution in the Cyclopentadienide Anion Serier", Tetrahedron, 1965, vol. 21, pp. 2313–2327.

*Primary Examiner*—P. Achutamurthy
*Attorney, Agent, or Firm*—David M. Bunnell

[57] ABSTRACT

Alkyl substituted cyclopentadienes are prepared by reacting cyclopentenones with a Grignard reagent followed by the acidification and dehydration of the resulting tertiary alcohol with an organic carboxylic acid.

9 Claims, No Drawings

PREPARATION OF ALKYLCYCLOPENTADIENES

The invention relates generally to the synthesis of substituted cyclopentadienes and more specifically to a process for making alkyl substituted cyclopentadienes from cyclopentenones by reacting the cyclopentenone with a Grignard reagent followed by the acidification and dehydration of the resulting tertiary alcohol with a carboxylic acid.

Alkyl substituted cyclopentadienes are used as monomers and in forming metallocenes of transition metals such as titanium, zirconium and hafnium. Such metallocenes are useful components of olefin polymerization catalysts, as is known in the art.

The synthesis of 1-methyl-3-alkylcyclopentadienes by the reaction of 3-methyl-2-cyclopentene-1-one with alkyl Grignard reagents such as methyl, ethyl or isopropyl magnesium halides, followed by alcohol formation and dehydration using strong acids such as HCl or p-toluene sulfonic acid is described in the literature. These processes give about a 50/50 mixture of endo and exo isomers. The exo isomers are not useful in forming metallocenes such that when such isomer mixtures are used in making metallocenes, the yield of metallocene is less than 50%. We have now disclosed a process which favors the formation of the desirable endo isomers.

In accordance with this invention there is provided a process for making an alkyl substituted cyclopentadiene, said process comprising reacting a cyclopentenone with an alkyl magnesium halide and then acidifying and dehydrating the resulting tertiary alcohol intermediate using an organic carboxylic acid, so as to form an alkyl substituted cyclopentadiene product which contains at least a 1.5/1 ratio of endo to exo isomers.

Cyclopentenones for use in the process of the invention can be prepared from 1,4-diketones by the process described in allowed copending U.S. application Ser. No. 08/016,447, now U.S. Pat. No. 4,276,199, whose disclosure is incorporated herein by reference. Such diketones have the formula $CH_3COCH_2CH_2COCH_2R$ where R is hydrogen or a hydrocarbyl group which contains 1 to 15 carbon atoms. Non-limiting examples of hydrocarbon groups include alkyl, substituted alkyl, aryl, substituted aryl, alkenyl, substituted alkenyl, and the like such as methyl, ethyl, propyl, isopropyl, butyl, isobutyl, tert-butyl, pentyl, hexyl, cyclohexyl, pentenyl, benzyl, phenyl, and naphthyl. Preferred cyclopentenones for use in the process are 3-alkylcyclopent-2-en-1-ones such as 3-methylcyclopent-2-en-1-one.

Non-limiting examples of alkyl magnesium halides (Grignard reagents) include $C_1$ to $C_{10}$ alkyl magnesium chlorides and bromides. Non-limiting examples of alkyl groups include methyl, ethyl, propyl, isopropyl, butyl, isobutyl, pentyl, hexyl and the like.

Non-limiting examples of organic carboxylic acids include formic acid, acetic acid, trifluoroacetic acid, trimethylacetic acid, propionic acid, butyric acid, benzoic acid and the like. Preferred are $C_1$ to $C_4$ alkyl carboxylic acids. Most preferred is acetic acid.

About equimolar portions of alkyl magnesium halide and cyclopentenone can be used, with the alkyl magnesium halide preferably used in about a 5 to 25% excess. The alkoxy magnesium halide intermediate is added to the carboxylic acid, preferably in water. The acid is preferably used in amounts of from about 1 to 3 mole per mole of intermediate, such that the pH is from about 1 to 7 and more preferably about 5.0.

According to a preferred mode of conducting the process, the cyclopentenone is slowly added to the alkyl magnesium halide in an inert solvent, such as an ether, a hydrocarbon or a mixture of such solvents. Non-limiting examples of suitable solvents include, diethyl ether, THF, toluene, glyme, diglyme and the like. The reaction temperature is kept at from about $-10°$ to $15°$ C., with cooling, and the reaction mixture is stirred for a time after the addition of the cyclopentenone to complete the reaction. About 1 to 5 hours is usually sufficient. The reaction mixture is then allowed to rise to ambient temperature. The alkoxy magnesium halide is slowly added into the organic carboxylic acid, preferably aqueous acetic acid, with cooling, at about $0°$ to $15°$ C. to form the alkyl substituted cyclopentadiene via a tertiary alcohol intermediate. After all the alkoxy magnesium halide has been added, the mixture is heated to from about $20°$ to $60°$ C. to complete the dehydration of the alcohol intermediate and the formation of the alkyl substituted cyclopentadiene product. The product collects in, and can be recovered from, the organic phase.

The process produces a major portion of endo isomers and usually a 2.5 to 1 or higher ratio of endo to exo isomers. In theory there are 5 possible endo and 3 possible exo isomers. The structure of one isomer of each type is illustrated below:

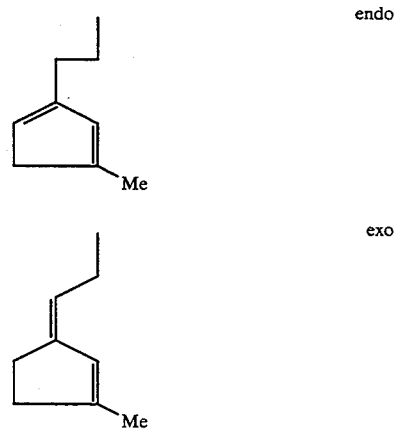

A representative reaction scheme is as follows:

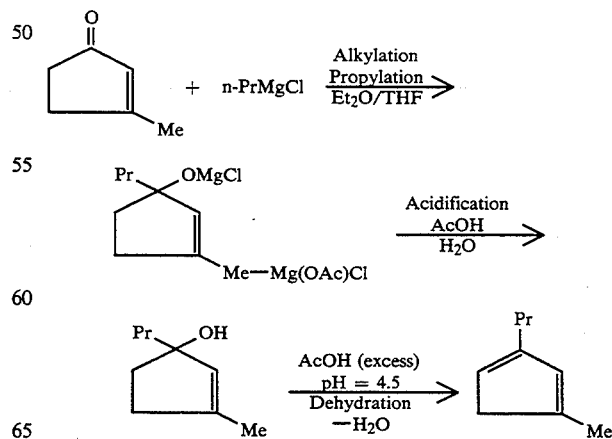

The invention is further illustrated by, but is not intended to be limited to, the following example.

Preparation of 1-Methyl-3-n-Propylcyclopentadiene n-PrMgCl (2.0M in Et$_2$O, 20 ml, 40 mmol) and THF (10 ml) were charged under nitrogen into a 100 ml, 3-necked, round-bottom flask equipped with a thermometer, magnetic stirring bar, and an addition funnel. The mixture was cooled to $-10°$ C. in an ice/acetone bath. 3-Methyl-2-cyclopentenone (97%, 3.6 g, 36.4 mmol) was added into the PrMgCl at $-10°$ to $-5°$ C. over a period of 20 minutes. The reaction mixture was slowly warmed to 22° C. over a period of one hour. GC analysis of a small acidified sample (added into excess aqueous acetic acid at 5° to 15° C., pH=4.5) showed a >97% conversion of 3-methyl-2-cyclopentenone. The reaction mixture was then slowly added at <5° C. into aqueous acetic acid (4.66 g, 77.6 mmol of acetic acid in 14.0 g of water) over a period of 30 minutes to form 1-methyl-3-n-propylcyclopentadiene via the dehydration of the 1-propyl-3-methyl-2-cyclopenten-1-ol intermediate. The pH of the aqueous layer was 4.5. The reaction mixture was stirred at 36° C. for 1 hour to complete the dehydration reaction. GC analysis indicated a >97% conversion of 1-propyl-3-methyl-2-cyclopenten-1-ol and the formation of 1-methyl-3-n-propylcyclopentadiene (with 28% exo isomers). The aqueous layer was phase cut. The organic layer, which weighed 29.2 g, was washed at 5° C. with aqueous Na$_2$CO$_3$ solution (2.42 g, 22.8 mmol of Na$_2$CO$_3$ in 10.0 g of water). The pH of the aqueous layer was 9.0. After phase cutting the aqueous layer, the organic layer weighed 25.4 g. Proton NMR (with CH$_2$Br$_2$ as internal standard) indicated that the yield of 1-methyl-3-n-propylcyclopentadiene was 77±4%. The structure of 1-methyl-3-n-propylcyclopentadiene was confirmed by GC/MS.

What Is claimed is:

1. A process for making an alkyl substituted cyclopentadiene, said process comprising, reacting a cyclopentenone with an alkyl magnesium halide under conditions to provide an alkoxy magnesium halide intermediate, combining said alkoxy magnesium halide intermediate with an organic carboxylic acid at a temperature of about $-10°$ to 15° C., the amount of said acid being sufficient to maintain a pH of from about 4.5 to 7.0, and then raising the temperature to from about 20° to 60° C. so as to dehydrate the resulting tertiary alcohol intermediate to a alkyl substituted cyclopentadiene product having a ratio of endo to exo isomers of at least 1.5/1.

2. The process of claim 1 wherein said cyclopentenone is a 3-alkylcyclopent-2-en-1-one and said alkyl substituted cyclopentadiene product is a 1,3-dialkylcyclopentadiene.

3. The process of claim 2 wherein said organic carboxylic acid is a C$_1$ to C$_4$ alkyl carboxylic acid.

4. The process of claim 3 wherein said organic carboxylic acid is aqueous acetic acid.

5. The process of claim 2 wherein said cyclopentenone is 3-methylcyclopent-2-en-1-one and said alkyl magnesium halide is a C$_1$ to C$_{10}$ alkyl magnesium chloride or bromide.

6. The process of claim 1 wherein said cyclopentenone is 3-methylcyclopent-2-en-1-one, said alkyl magnesium halide is n-propyl magnesium chloride and said product is 1-methyl-3-n-propylcyclopentadiene which contains at least a 2.5/1 ratio of endo to exo isomers.

7. The process of claim 1 wherein the acid is used in an amount of from about 1 to 3 mole per mole of intermediate.

8. The process of claim 7 wherein the acid is used in an amount to provide a pH of about 4.5.

9. The process of claim 1 wherein the alkoxy magnesium halide intermediate and acid are combined at a temperature of from about 0° to 15° C.

* * * * *